(12) United States Patent
Huschmand Nia et al.

(10) Patent No.: US 8,501,109 B2
(45) Date of Patent: Aug. 6, 2013

(54) DISINFECTION SYSTEM

(75) Inventors: Abdolhamid Huschmand Nia, Pirmasens (DE); Reinhold Wegener, Goettingen (DE)

(73) Assignee: Georg-August-Universtaet Goettingen, Goettingen (DE)

( * ) Notice: Subject to any disclaimer, the term of this patent is extended or adjusted under 35 U.S.C. 154(b) by 939 days.

(21) Appl. No.: 12/052,022

(22) Filed: Mar. 20, 2008

(65) Prior Publication Data

US 2008/0226507 A1 Sep. 18, 2008

Related U.S. Application Data

(63) Continuation-in-part of application No. PCT/EP2006/009166, filed on Sep. 20, 2006.

(60) Provisional application No. 60/718,299, filed on Sep. 20, 2005.

(51) Int. Cl.
| | | |
|---|---|---|
| *A61L 2/00* | (2006.01) | |
| *A61L 9/00* | (2006.01) | |
| *B65D 83/10* | (2006.01) | |
| *B65D 73/00* | (2006.01) | |
| *B65D 83/04* | (2006.01) | |
| *B65D 85/42* | (2006.01) | |

(52) U.S. Cl.
USPC ........... 422/300; 422/292; 206/361; 206/362; 206/469; 206/532

(58) Field of Classification Search
USPC ................. 422/292, 300; 206/361, 362, 469, 206/532; 20/469, 532
See application file for complete search history.

(56) References Cited

U.S. PATENT DOCUMENTS

| | | | |
|---|---|---|---|
| 3,613,685 A | | 10/1971 | Reynolds |
| 3,888,629 A | * | 6/1975 | Bagshawe ...................... 436/541 |
| 5,042,690 A | * | 8/1991 | O'Meara .......................... 222/83 |
| 5,209,909 A | * | 5/1993 | Siegel et al. .................. 422/292 |
| 5,288,159 A | * | 2/1994 | Wirt ................ 401/133 |
| 5,335,855 A | * | 8/1994 | Borod ............ 239/152 |
| 5,622,764 A | * | 4/1997 | Battles ............ 428/52 |
| 5,660,273 A | * | 8/1997 | Discko, Jr. ..................... 206/229 |
| 6,248,085 B1 | * | 6/2001 | Scholz et al. ..................... 604/2 |
| 6,270,275 B1 | | 8/2001 | Martz |
| 6,488,665 B1 | * | 12/2002 | Severin et al. ................ 604/200 |
| 6,520,326 B2 | * | 2/2003 | McIvor et al. ................ 206/305 |
| 6,779,657 B2 | * | 8/2004 | Mainwaring et al. ......... 206/229 |
| 2002/0004942 A1 | * | 1/2002 | Bryan .......................... 800/288 |
| 2009/0255953 A1 | * | 10/2009 | May et al. ......................... 222/1 |

FOREIGN PATENT DOCUMENTS

| | | |
|---|---|---|
| JP | 2004 001784 A | 1/2004 |
| WO | WO 98/38954 A2 | 9/1998 |

* cited by examiner

*Primary Examiner* — Regina M Yoo
(74) *Attorney, Agent, or Firm* — Whitham Curtis Christofferson & Cook, PC

(57) ABSTRACT

The present invention relates to a disinfection system, arrangement comprising at least two sequentially arranged disinfection systems and containers comprising various chambers usable for the disinfection system. In particular, the present invention relates to a disinfection system comprising at least one chamber adapted for containing at least one first chamber adapted to contain disinfectant and at least one second chamber adapted to contain at least one swab and/or sponge, said at least one swab and/or sponge and additional separated space for taking up the disinfectant. The system is designed such that a predetermined amount of disinfectant is brought into contact with the at least one swab and/or one sponge immediately before use.

22 Claims, 15 Drawing Sheets

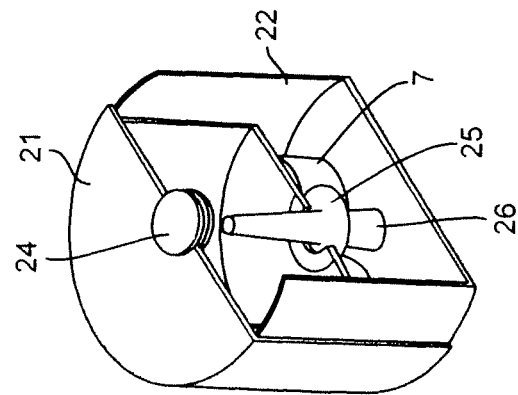
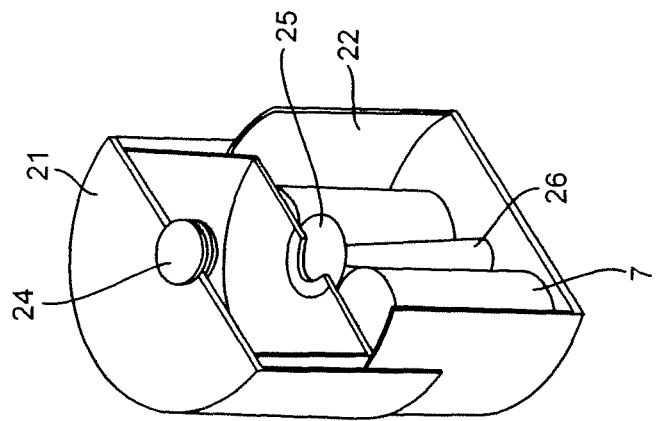
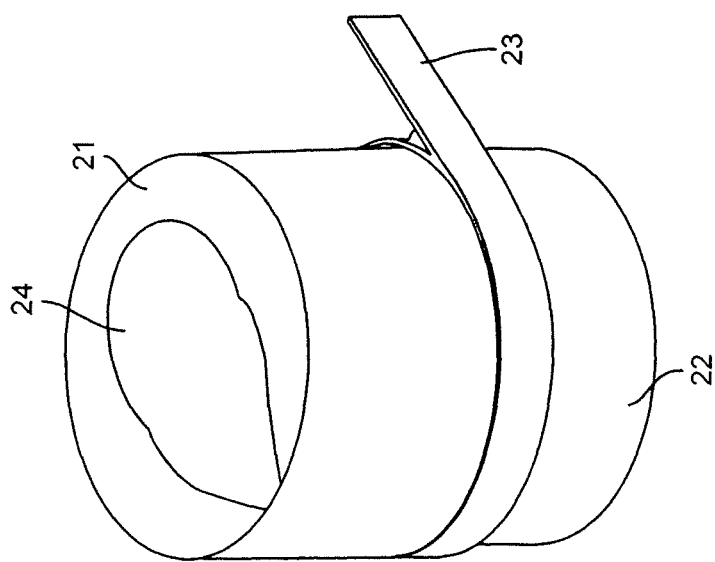
Figure 7C
Figure 7B
Figure 7A

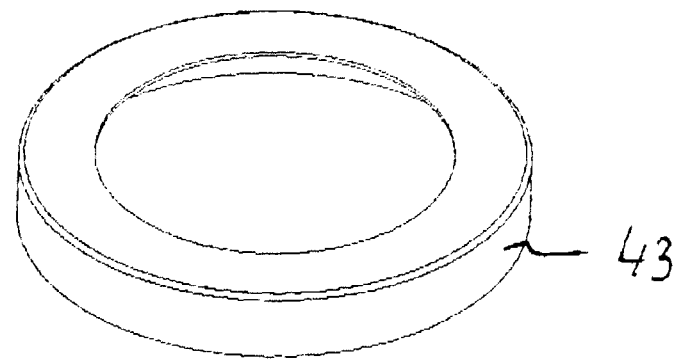
Figure 9A
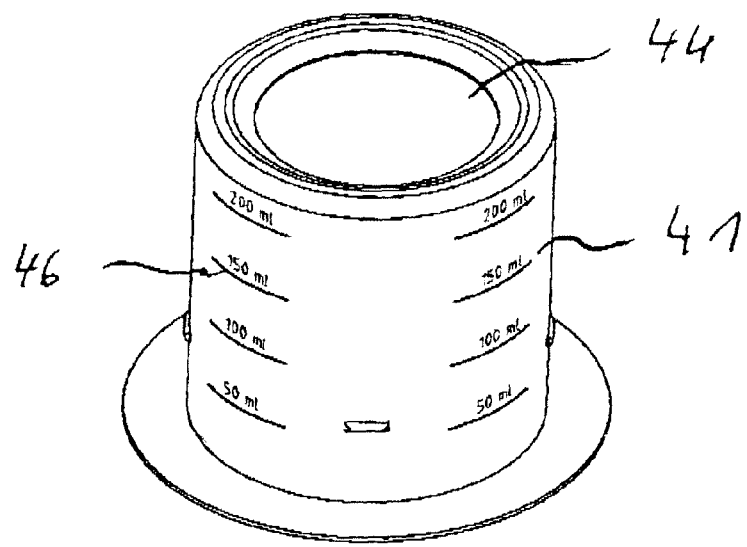
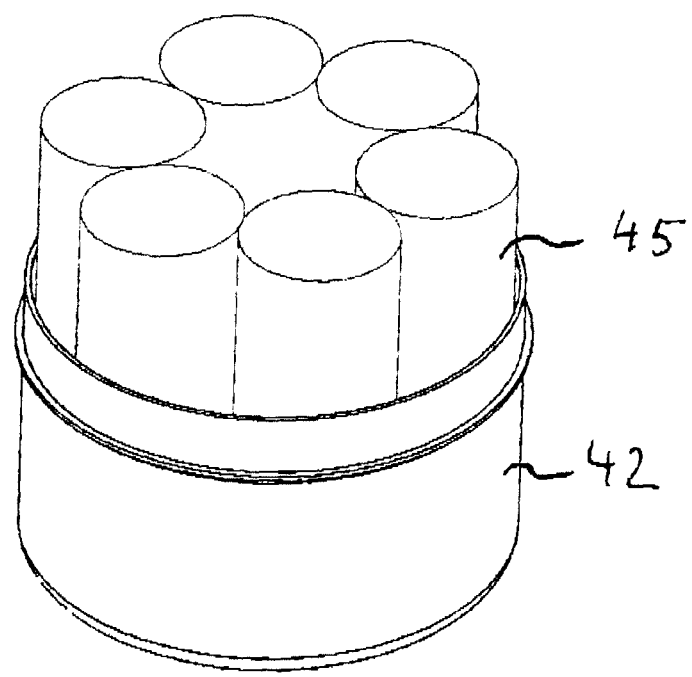

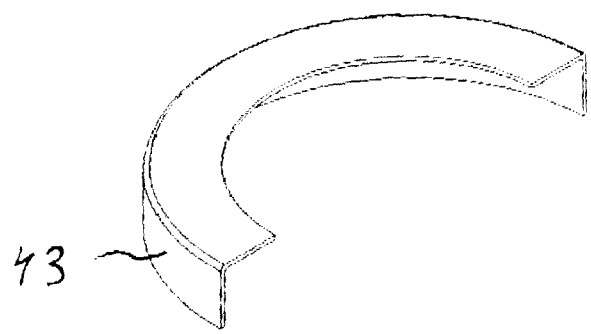
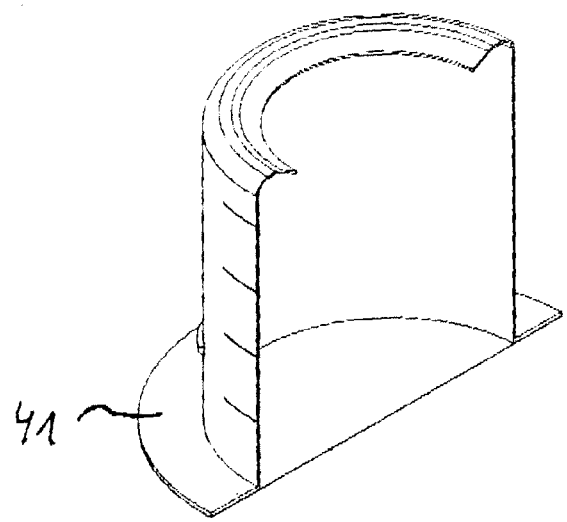
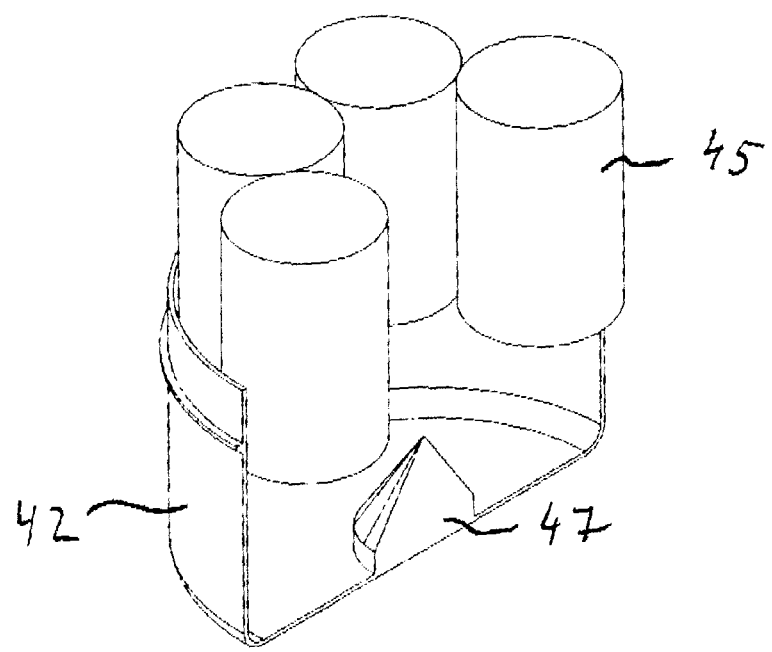
Figure 9D

DISINFECTION SYSTEM

CROSS-REFERENCE TO RELATED APPLICATIONS

This application is a continuation-in-part (CIP) of PCT/EP2006/009166 filed Sep. 20, 2006, which claims priority to U.S. Patent Application 60/718,299 filed Sep. 20, 2005.

The present invention relates to a disinfection system, arrangements comprising at least two sequentially arranged disinfection systems and containers usable for the disinfection system. In particular, the present invention relates to a disinfection system comprising at least one first chamber adapted to contain a disinfectant and at least one second chamber adapted to contain at least one swab and/or sponge, said at least one swab and/or sponge and additional separated space for taking up the disinfectant. The container is designed such that a predetermined amount of disinfectant is brought into contact with the at least one swab and/or one sponge immediately before use.

BACKGROUND

Disinfection of skin or wounds is necessary before further handling or treatment of the same. In clinical applications, such as in surgery disinfection of the area to be treated, e.g. of the skin, is essential. Usually, before surgery the disinfection of skin is conducted as follows. As a preliminary cleaning step, the skin is treated with wash lotions or solutions the day before. In the operation theatre a disinfectant is applied with sterile swabs to the area where incision is to be performed and to the surrounding skin. The disinfection is applied at least two times for several minutes to ensure complete disinfection. Afterwards, the excessive disinfectant is removed with dry sterile swabs.

In practice the surgeon or the nurse puts an undefined number of sterile swabs in a bowl containing an undefined amount of disinfectant. The swabs are taken out of the bowl with a forceps one by one and are used for applying the disinfection to the skin surface. In case the disinfectant in the bowl or the number of swabs is not sufficient to cover the whole surface area twice, additional soaked swabs have to be prepared with disinfectant as necessary.

Thus, the pre-surgical disinfection of the skin surface is a laborious work which is not standardized and in all probability will be handled differently in each institution. Further, it is neither possible to define the volume of the disinfectant nor the number of swabs needed for the disinfection of a certain area of the skin. Therefore, the presently conducted method for pre-surgical disinfection is time consuming, costly and non-standardized. Moreover, since usually the swabs or sponges are saturated with more disinfectant than necessary, the disinfectant tends to flow down or drop down from the skin and, therefore, must be absorbed by adsorbing material. Furthermore, the disinfectant may drop on the floor which may lead to slipping of staff.

Since, in Germany more than one million infections per year occur in hospitals disinfection and/or sterilization is a major point in surgery and other treatments involving a surgical intervention. Moreover, some 20% of the infections occurring in hospitals are due to post-surgical wound infections. This is in part due to undefined standards for skin disinfection.

Therefore, the aim of the present invention is the provision of a disinfection system allowing a defined, comparable and inexpensive disinfection of skin and wounds, thus, not only reducing the costs but also the risk of post-surgical wound infections.

SUMMARY OF THE PRESENT INVENTION

The present invention relates to a disinfection system comprising at least two separate chambers, i.e. at least one first chamber being adapted to contain a disinfectant and at least one second chamber being adapted to store at least one swab and/or one sponge. The chambers are designed such that the disinfectant can be directly or indirectly introduced into the second chamber containing at (east one swab and/or one sponge, such that the at least one sponge and/or swab can be impregnated with a predefined volume of disinfectant each.

The disinfection system according to the present invention allows the provision of a defined number of swabs and/or sponges each impregnated with a defined amount of disinfectant. Thus, a standardized sterilization of skin and/or wounds is possible.

Further, the present invention relates to arrangements comprising at least two sequentially arranged container systems.

In addition, the present invention relates to the container of the disinfection system.

BRIEF DESCRIPTION OF THE DRAWINGS

FIG. 7 is a perspective view of a further preferred embodiment of the present invention. FIG. 7a shows the system of a first chamber and a second chamber with means for protecting undesired moving of the slidably connected chambers.

The first chamber and the second chamber are designed to interlock with each other. As shown in FIG. 7b in a first position, the first chamber is mounted on the second chamber containing the swabs and the chambers are transversally movable connected. The first chamber has two openings covered with a movable cover and a cover which can be penetrated. FIG. 7c shows the system in a second position where the two chambers have been pressed such that the pin present in the second chamber penetrated the cover of the first chamber. After depression of the chambers disinfectant present in the first upper chamber can flow into the second, lower chamber and the swabs present in the lower chamber are impregnated with the disinfectant uniformly.

FIG. 8 shows an exploded drawing of said embodiment with a first chamber and a second chamber containing swabs as well as a means for covering and connecting the first with the second chamber.

FIG. 7c shows the system in a second position where the two chambers have been pressed in the second position. In the second position the pin present in the second chamber, see cross sectional view FIG. 9d, penetrated the bottom of the first chamber, see cross section of the perspective view shown in FIG. 9e. After depression of the chambers, disinfectant present in the first upper chamber can flow into the second, lower chamber and the swabs present in the lower chamber are impregnated with the disinfectant uniformly.

DETAILED DESCRIPTION

Figure 1A:
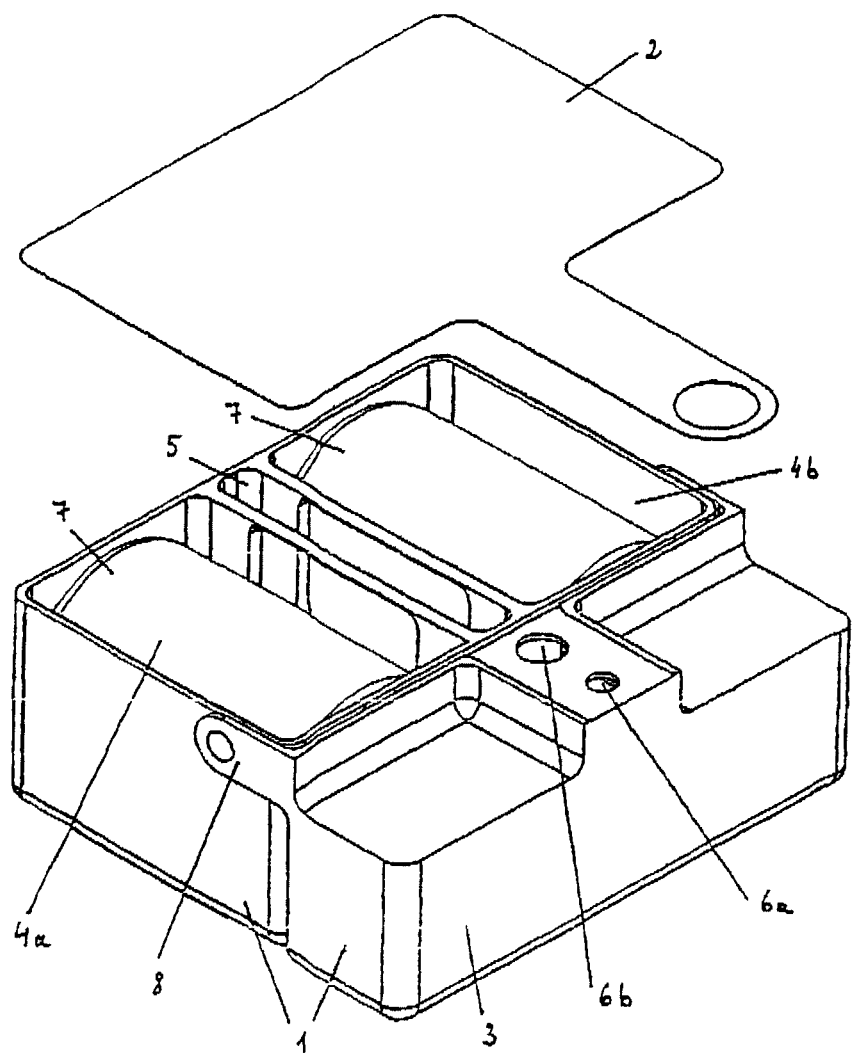
In FIG. 1a a first chamber adapted to contain the disinfectant and two second chambers each containing a swab are shown. The first chamber being arranged in a manner that the disinfectant can be poured into the second chamber in a free space between the two sponges by turning relatively the first chamber towards the second chamber, as shown in FIG. 1b.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described.

In accordance with the present invention a disinfection system is provided. The disinfection system according to the present invention comprises (i) at least one first chamber and at least one second chamber whereby the at least one first chamber being adapted to contain a disinfectant and the at least one second chamber being adapted to store at least one swab and/or one sponge (ii) at least one swab and/sponge present in the at least one second chamber and optionally iii) disinfectant characterized in that the at least one first chamber and the at least one second chamber are designed such that they are removably connectable to each other and such that the disinfectant can be directly or indirectly introduced into the at least one second chamber adapted for containing the at least one swab and/or one sponge when the chambers are jointly connected with means for introducing the disinfectant from the at least one first chamber into the at least one second chamber.

In a preferred embodiment the disinfection system contains at least two swabs and/or sponges, and preferably between three to seven swabs and/or sponges.

The swabs and/or sponges are composed of cotton material and/or foam plastic or the like.

Thus, the disinfection system is designed to contain a sufficient number of swabs and/or sponges and the corresponding volume of disinfectant for the disinfection of a certain skin area.

In another embodiment, the disinfection system comprises at least one third chamber adapted to contain at least one swab and/or at least one sponge. This at least one third chamber is designed such that no disinfectant can be introduced into said chamber, thus, leaving dry sponges or dry swabs useful for drying the surface area or the wound area after disinfection with the liquid disinfectant. Thus, the disinfection system includes all materials necessary for patient preparation, e.g. for pre-surgical preparation.

The at least one first chamber and the at least one second chamber may be in the form of a one piece container or in form of a multi-part container, e.g., it may comprise two separate containers which are connected with each other.

The chambers or the containers are composed of any suitable material which can be sterilized. For example, the chambers or containers are composed of a plastic material like polyethylene (PE), polypropylene (PP), polystyrene (PS) or other polymers or copolymers useful to form sterilizable chambers or containers.

In one aspect of the invention, the at least one chamber adapted for containing the disinfectant and the at least one chamber adapted to contain the swab and/or sponge are separated by a common wall. The common wall functions as a means for introducing the disinfectant from the at least one first chamber into the at least one second chamber and has a weakened portion or a weak line which is capable of forming a through-hole or passage between said chambers. That is, via the weakened region forming a through-hole or passage between the chambers, after extraneous cause or after penetration with a protrusion which may have a conical form present in one of the chambers, the disinfectant can be transferred from the at least one first chamber being adapted for containing a disinfectant into at least one of the second chamber storing at least one swab and/or one sponge. For example, the weakened region may be easily penetrated in comparison with neighboring area where there is no such weakening.

Thus, in one embodiment the at least one second chamber adapted to store at least one swab and/or one sponge is designed to have protrusion(s) arranged to penetrate the common wall between at least one first chamber adapted to contain the disinfectant and the at least one of the second chamber(s) adapted to contain the swabs and/or sponges. When penetrating the common wall, preferably in weakened portions or at a weak line or having a predetermined or preformed breaking point, a predetermined amount of disinfectant flows from the at least one first chamber into at least one of the at least one second chamber through the through-hole or passage formed by penetration. In addition, construction of the common wall and the area of the second chamber where the protrusion(s) is/are arranged allows complete transfer of the disinfectant from the at least one first chamber to the at least one second chamber. This ensures that each swab or sponge present in each of the second chambers is impregnated with the same amount of disinfectant. The protrusions may have a conical form.

Hence, in another preferred embodiment, the at least one second chamber adapted to contain the swabs and/or sponges is designed to have protrusion(s) or pin(s) arranged so as to be capable of penetrating a wall of the chamber containing the disinfectant. In a particular embodiment thereof, each of the first chambers adapted to contain the disinfectant are relatively movable to the second chamber(s) adapted to contain the swabs and/or sponges from a first position into a second position whereby when moving each of the chambers from the first to the second position the protrusion(s) or pin(s) penetrate(s) the wall of the at least one first chamber adapted to contain the disinfectant. Thus, the disinfectant can flow into the at least one second chamber adapted to contain the swabs and/or sponges. In case at least one third chamber adapted to contain at least one swab and/or at least one sponge is present in the container, protrusion(s) and/or pin(s) are not located in said chambers. In addition, the walls of the at least one third chamber are designed to be impervious to fluids, in particular to any disinfectant.

When each of the at least one first chamber containing the disinfectant is relatively movable to the second and/or third chamber, each of the at least one first chamber adapted to contain the disinfectant can be locked in a first and a second position. That is, each of the at least one first chamber has protrusions or notches to lock the chambers at predetermined positions. Thus, a clamping mechanism allows locking each of the relatively movable at least one first chamber adapted to contain the disinfectant in a first or a second position. When moving the at least one first chamber from the first position to the second position the protrusion(s) of the at least one second chamber penetrates the wall of the at least one first chamber forming through-holes or passages. The area of the at least one second chamber where the protrusion(s) or pin(s) are arranged is a pivoted area allowing the flow of the disinfectant to the other part of the at least one second chamber where the at least one swab or sponge is located.

In a further aspect of the present invention the at least one first chamber and the at least one second chamber of the system are separated by a common wall which functions as a means for introducing the disinfectant from the at least one first chamber to the at least one second chamber. The common wall has at least one opening which is closed in a first position but open in a second position for introducing the disinfectant into the at least one second chamber. In this embodiment, the chambers are in the form of a one piece container. In a preferred embodiment each of the at least one openings is closed with a cover in the first position. The cover is connected with the lid of the one piece container. Detaching the lid from the container brings the disinfection system into the second position so that the disinfectant can flow through the opening from the at least one first chamber to the at least one second chamber.

In an additional embodiment the means for allowing the flow of the disinfectant from the first chamber to the second chamber can be a pivoting connection. That is, the disinfectant may flow into the second chamber from the first chamber when bending relatively the at least one first chamber or the at least one second chamber to the at least one second chamber or the at least one first chamber, respectively.

Additionally, the present invention relates to a disinfection system characterized in comprising at least two first chambers adapted for containing disinfectant, with at least two different fluids being contained in different first chambers wherein at least one of the two different fluids is a disinfectant. Thus, one chamber of said first chambers may contain a washing solution to clean the skin surface or the wound first and the second first chamber may contain the disinfectant. Alternatively, at least two different disinfectants may be contained in the at least two first chambers.

Since the disinfection system shall be used in e.g. presurgical operations, it necessitates that the disinfection system and the various materials contained therein are present in a sterile form. Thus, preferably a detachable lid of the disinfection system hermetically seals the chambers. The hermetically sealed chamber lid assembly allows that the system can be sterilized and/or autoclaved.

Further, the disinfectant of the disinfection system according to the present invention may be provided in a second container or box adapted for external supplying the disinfectant into the first container in a predetermined amount.

To identify whether the disinfection system according to the present invention underwent sterilization, the disinfection system may additionally comprise an element for displaying the status of sterilization, like a tag, etc.

Thus, the disinfection system according to the present invention may be adapted to be a system for single use.

Another aspect of the invention is an arrangement comprising at least two sequentially arranged disinfection systems according to the present invention for packaging or shipping.

Further, the present invention relates to a one piece container or a multi part container comprising at least one first chamber and at least one second chamber as described herein of the disinfection system.

The present invention is now described in further detail with reference to the accompanying drawings. Corresponding or equivalent elements of the present invention illustrated into the drawings are designated with the same numerals.

Figure 1B:
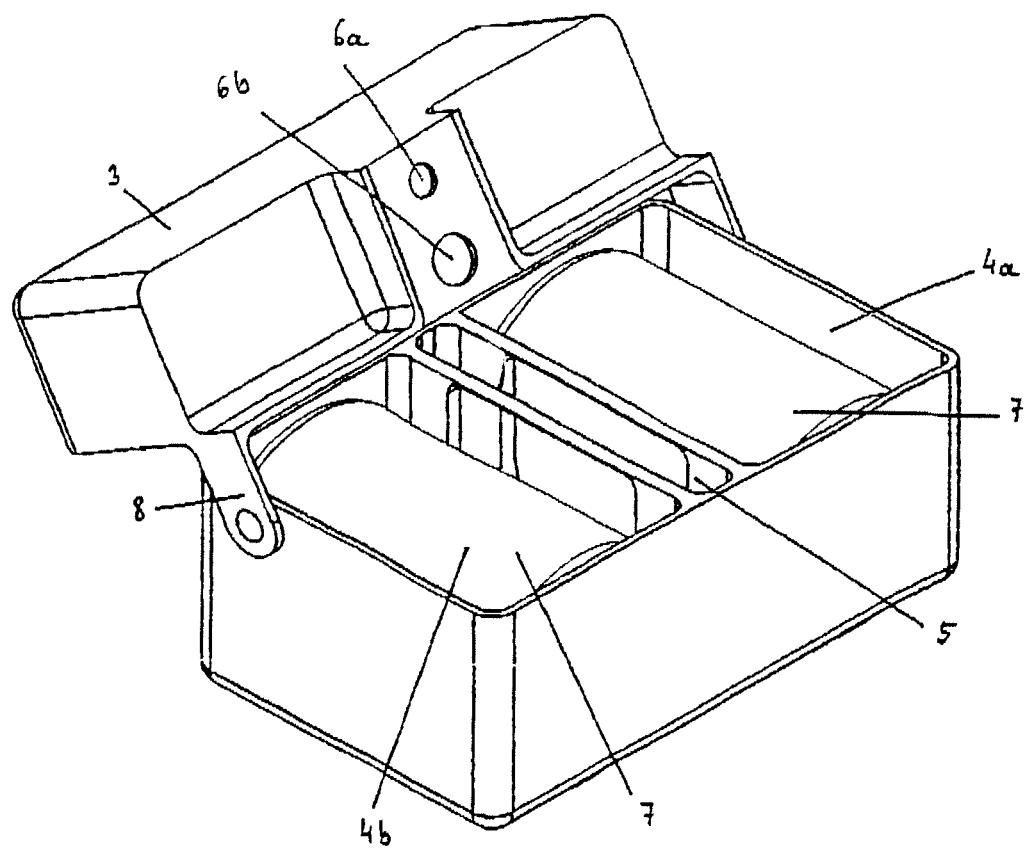
FIG. 1 illustrates a first embodiment of the present invention.

FIGS. 1a and 1b show a disinfection set according to a first embodiment of the present invention. The disinfection system comprises a container 1 with a detachable lid 2. The container 1 has various separate chambers which may be interconnected by through-holes or passages. In particular, the container has a first chamber 3 adapted to contain the disinfectant and two second chambers, 4a and 4b, adapted to contain a sponge or swab 7. In between the two second chambers an additional first chamber 5 is arranged wherein the disinfectant will be introduced when the first chamber 3 is brought into the second position, see FIG. 1b. Moreover, openings 6a and 6b are present in the first chamber 3. The first chamber 3 is relatively movable to chambers 4 and 5 with means 8 for swivelling the first chamber from the first position to the second position in order to introduce the disinfectant from the first chamber 3 into the additional first chamber 5. From chamber 5 a predetermined amount of the disinfectant will flow into the second chambers 4a and 4b. The disinfectant will impregnate the swabs 7 present in the second chambers and the physicians doing the sterilization of the skin and wound can use sterile swabs or sponges with predetermined amounts of disinfectant.

Figure 2:
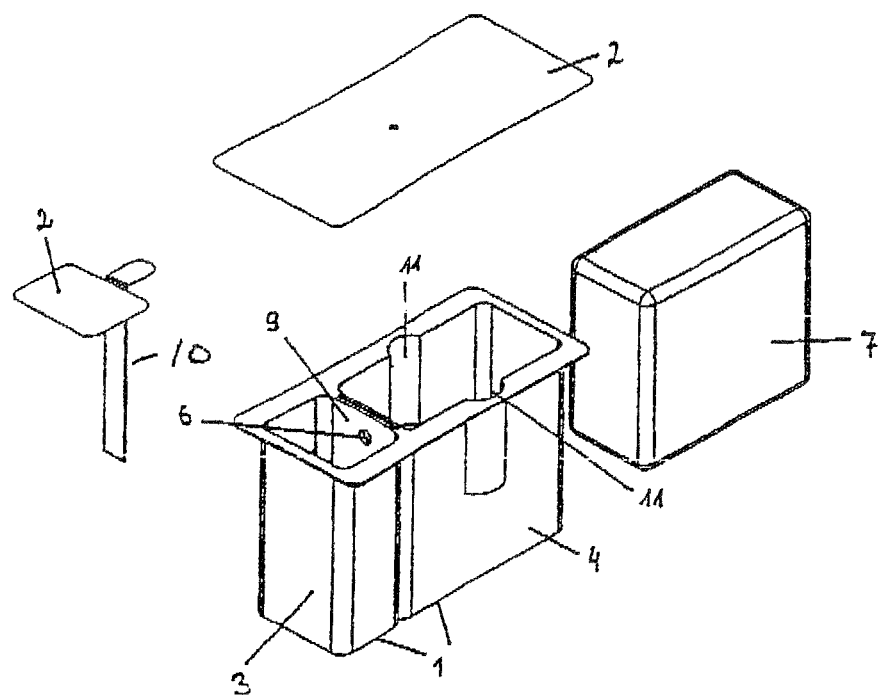
FIG. 2 illustrates a second embodiment of the present invention. Said embodiment has an opening between the first chamber and the second chamber which can be opened by peeling off the cover sealing both chambers.

FIG. 2 shows a further embodiment of the present invention. The container 1 has two chambers, one first chamber 3 and one second chamber 4. The first chamber 3 and the second chamber 4 are separated by a common wall 9. The common wall 9 comprises means for introducing the disinfectant from the first chamber into the second chamber, i.e. openings 6. The openings 6 are closed with a cover 10 in a first position and the cover 10 is removed from the openings 6 in a second position. Preferably, the cover 10 is connected with the lid 2 of the container 1. That is, in the first position, the lid 2 covers the whole container 1, and, preferably, hermetically seals the container 1. When bringing the lid 2 from the first into the second position, the lid 2 is detached from the container 1 and, simultaneously, the cover 10 is removed from the openings 6, since the cover is operatively connected with the lid 2. The disinfectant present in the first chamber 3 can flow from the first chamber 3 into the second chamber 4 through the openings 6 in the second position. Preferably, the container 1 has curved portions 11, preferably in the top third of the side walls of the second chamber 4, to allow the physician to take out the soaked swab or sponge 7 with e.g. a forceps. In FIG. 2, the swab is shown outside of the second chamber 4.

Figure 3:
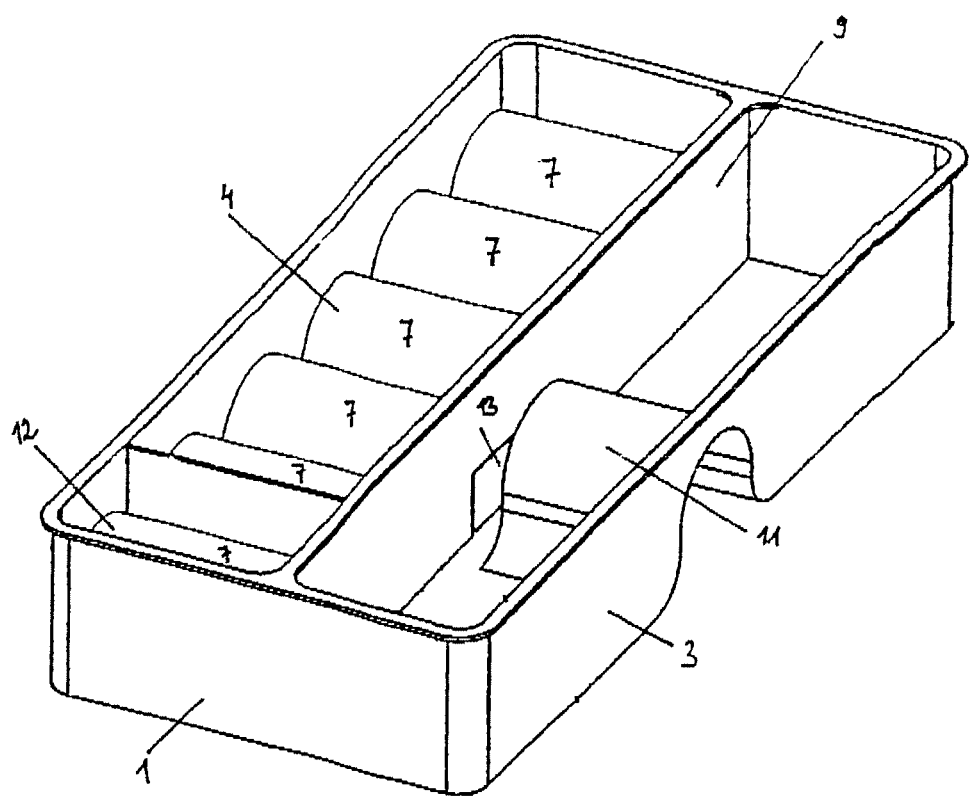
FIG. 3 illustrates a further embodiment of the present invention. Therein the means for introducing the disinfectant from the first chamber into the second chamber is a weakened portion of the common wall separating both chambers which may form an opening after applying external forces.

FIG. 3 shows another embodiment of the disinfection system according to the present invention. This embodiment comprises essentially the same components of the disinfection system as described above. In particular, provided is a container 1, comprising a first chamber 3, a second chamber 4 containing five swabs 7 and a third chamber 12 containing one swab 7. The common wall 9 between the first chamber 3 and the second chamber 4 comprises a weakened region 13 which is capable of forming a through-hole or passage between said first chamber 3 and said second chamber 4. The walls 14 between the third chamber 12 and the first and second chamber 3, 4 are designed to prevent the flow of any disinfectant or other liquid from the first or second chamber 3, 4 into the third chamber 12.

The first chamber 3 is designed to have a recessed portion 11. Further, the weakened region 13 of the common wail 9 between the first chamber 3 and the second chamber 4 is opposite to the recess in the first chamber 3. In addition, the outer wall of the first chamber facing the weakened region of the common wall 13 of the first chamber 3 and the second chamber 4 is flexible insofar that by extraneous forces the weakened region 13 can be broken and the disinfectant present in the first chamber 3 can flow into the second chamber 4. Thus, a predetermined amount of disinfectant can flow into the second chamber 4 and the swabs 7 present in the second chamber 4 are impregnated with the disinfectant.

FIGS. 4a to c show a further embodiment of the disinfection set according to the present invention. FIG. 4a is a perspective view of a container 1 comprising a box of first chambers 3, second chambers 4 and a third chamber 12. The box comprising the first chambers 3 is an insert which can be inserted into regions of the second chambers 4. Normally, the insert comprising the first chambers 3 are looked in a first position, see FIG. 4b. The insert possesses protrusions 15 which are locked in the notches 17 present in the outer wall of the container 18. When the swabs or sponges shall be impregnated with the disinfectant, the insert is moved from the first position into the second position, see FIG. 4c.

Figure 4:
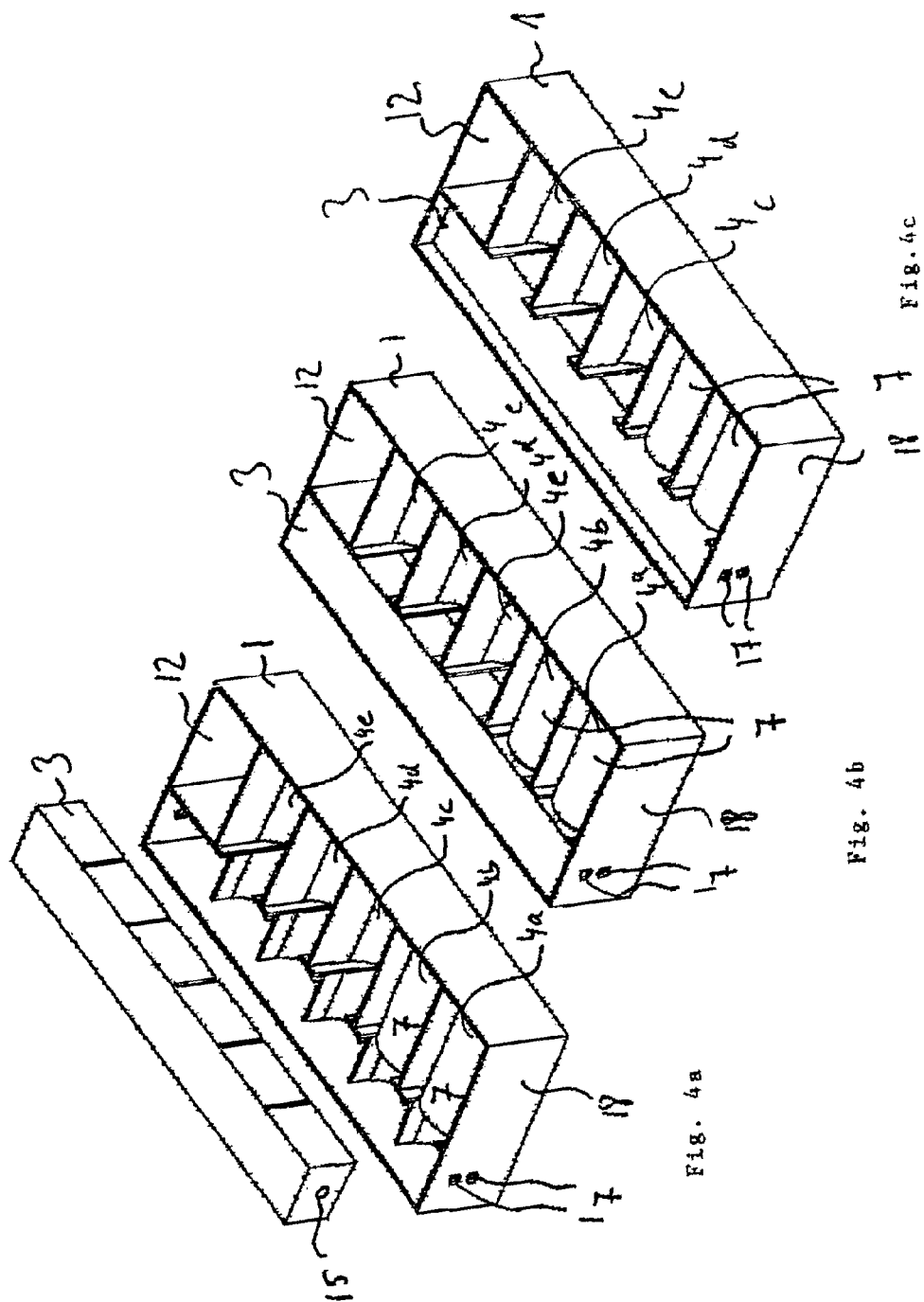
FIG. 4 illustrates a further preferred embodiment of the present invention. Shown is a container in which sponges are arranged in second chambers completely separated from each other. The disinfectant is portioned in a series of first chambers in an insertable box. The disinfectant can flow into the second chambers containing sponges after one wall of the box having a series of first chambers is perforated by pins on the bottom of the second chambers.
Figure 5:
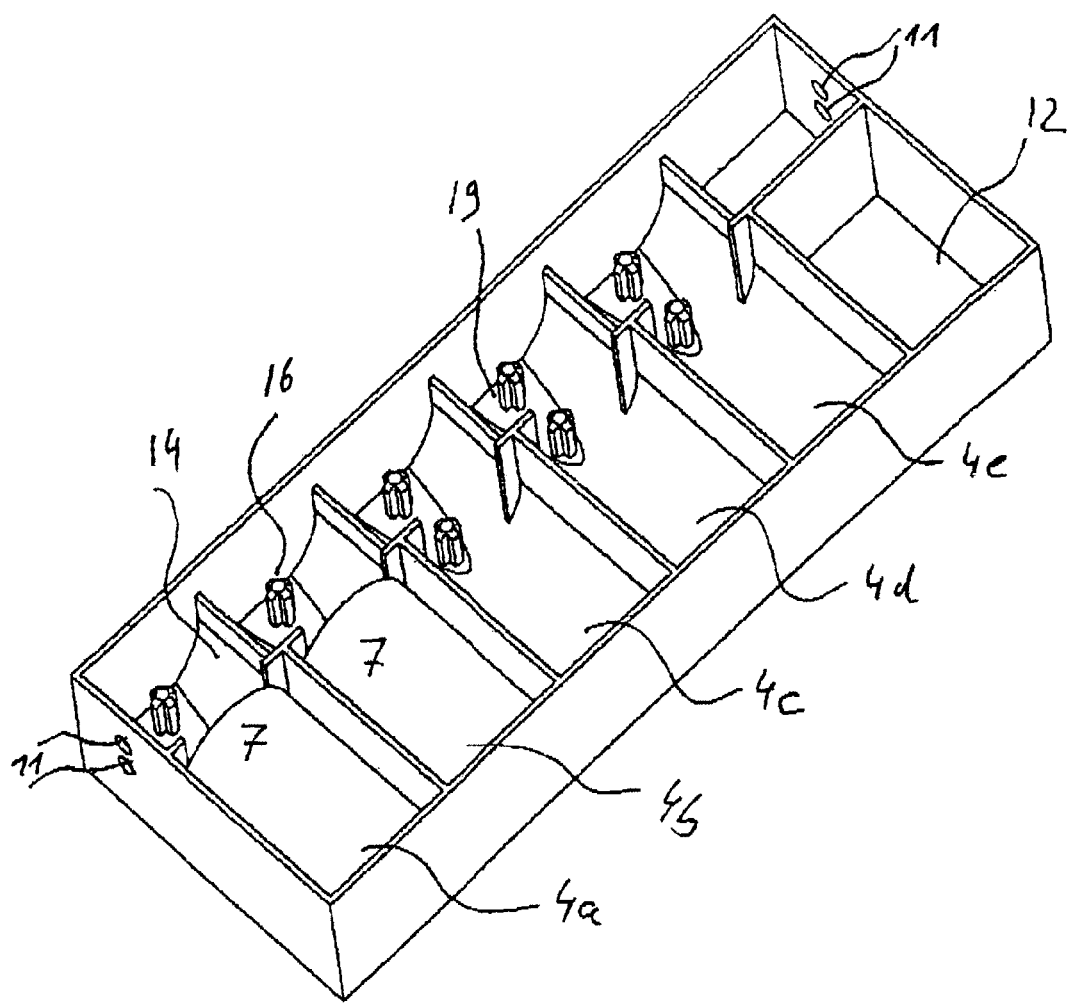
FIG. 5 is a further perspective view of the embodiment shown in FIG. 4.

FIG. 5 is a perspective view of the container shown in FIG. 4 without the insert comprising the first chambers. Shown are protrusions 16 in one area of the second chamber 4 and the swabs 7 present in the second chambers. The separating walls 14 which represent the extensions of the separating walls between each of the second chambers 4 are designed to allow a guidance of the insert. In a preferred embodiment, the extensions and the separating walls 14 between the different second chambers 4 allow the separation of each of the second chambers in such a way that different liquids can be introduced into the second chambers.

The protrusions 16 present in one region of the second chambers penetrate the lower wall of the insert comprising the first chamber(s) when moving the insert from the first position to the second position. The regions where the protrusions 16 are located are pivoted 19, thus, securing the flow of the whole amount of disinfectant to the region where the protrusions are located to the region where the swaps are stored.

The third chamber 12 has no connection to the second or first chamber. In addition, the third chamber does not have any protrusions or pins which may penetrate the wall of the first chambers. Thus, the swab present in the third wall will not be impregnated with any liquid but can be used for drying the sterilized region.

Figure 6A:
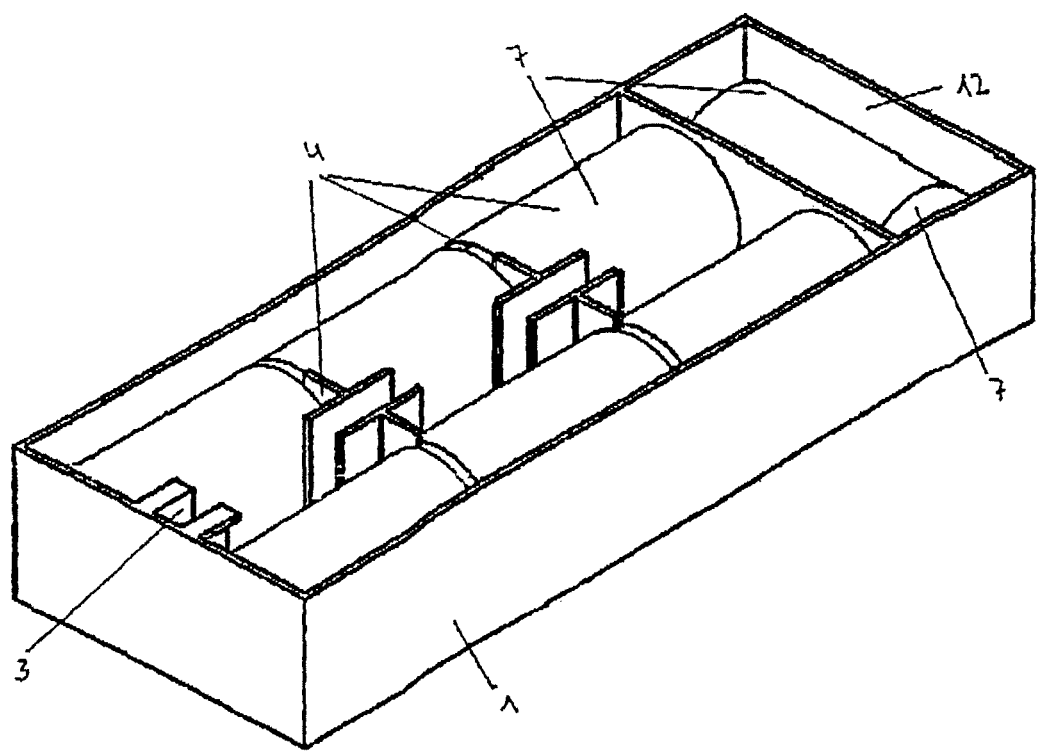
As shown in FIG. 6a the sealing cover has a small opening which can be peeled of separately allowing the box to remain covered until the swabs have been soaked with the disinfectant introducible through the small opening into the free space between the two rows of swabs. The remaining cover is than peeled off from the other end of the box.
Figure 6B:
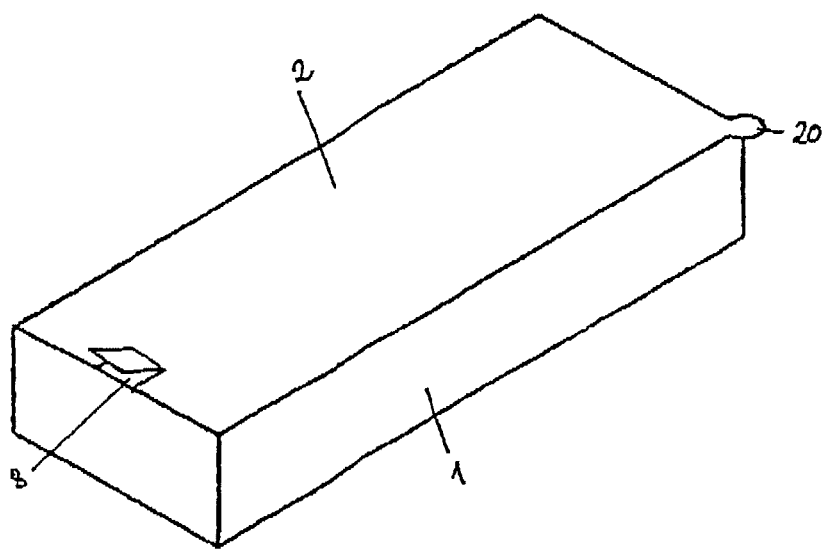
FIG. 6 illustrates parts of another preferred embodiment of the present invention. Shown is a system comprising first, second chambers and third chambers adapted to contain swabs, which can be sealed with a detachable lid, see FIG. 6b.

FIG. 6 provides details of a further embodiment of the present invention. In particular, FIG. 6a shows a container comprising second chambers 4 and a third chamber 12 adapted for containing swabs 7, which can be sealed with a detachable lid 2 as shown in FIG. 6b. The sealing lid or cover has a small opening 8 which can be peeled of separately allowing the box to remain covered until the swabs have been soaked with the disinfectant introducible through the small opening 8 into the chamber 3 arranged between the two rows of swabs. The remaining lid 2 is than peeled off from the other end of the box with the help of a flap 20. In this embodiment, the disinfectant is supplied in a predetermined amount from external sources, e.g. from an additional container containing the predetermined amount of the disinfectant which is part of the disinfection system according to the present invention (not shown).

FIG. 7 shows another preferred embodiment of the present invention.

FIG. 7a shows the system of a first chamber 21 and a second chamber 22 with means 23 for protecting undesired moving of the slidably connected chambers. As shown in FIG. 7b in a first position, the first chamber is mounted on the second chamber containing the swabs and the chambers are transversally movable connected. The first chamber has two openings covered with a removable cover 24, e.g. a lug, and a cover 25 which can be penetrated, respectively. The opening 25 to be penetrated may be composed of material resistant to the disinfectant but easily breakable, e.g. plastic foils, which are well known in the art, thus allowing easy penetration when relatively moving the chambers. The opening 24, e.g. the lug, is designed to allow introducing a predetermined amount of disinfectant into the first chamber 21. Of course, the disinfectant is introduced into the first chamber 21 before penetrating said chamber, thus, forming a passage or through-hole between the first chamber 21 and the second chamber 22. The second chamber has one or more protrusions 26 which are preferably of conical shape as shown in FIGS. 7a and 7b.

FIG. 7c shows the system in a second position where the two chambers have been pressed such that the pin 26 present in the second chamber 22 penetrated the cover 25 of the first chamber 21. After depression of the chambers disinfectant present in the first upper chamber 21 can flow into the second, lower chamber 22 and the swabs 7 present in the lower chamber are impregnated with the disinfectant uniformly (not shown).

Figure 8:
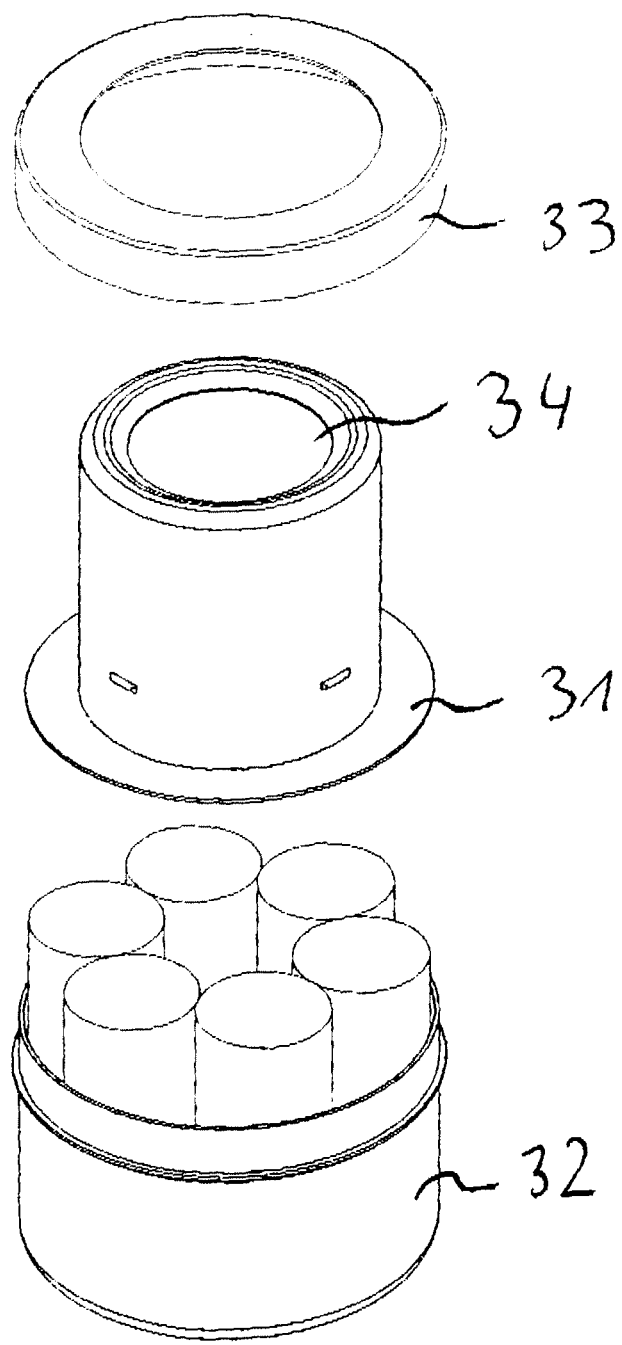
FIG. 8 is a perspective view of a further preferred embodiment of the present invention.

In FIG. 8 a further preferred embodiment of the present invention is provided.

FIG. 8 is an exploded drawing showing a perspective view of a first chamber 31 and a second chamber 32 with means 33 for covering and protecting undesired moving of the slidably connected chambers. In the second chamber 32 swabs are present which may be impregnated with disinfectant. The second chamber 32 has a pin (not shown) allowing penetration of the bottom of the first chamber after pressing the first chamber into the second chamber. Similar to the embodiments above, the bottom of the first chamber 34 to be penetrated may be composed of material resistant to the disinfectant but easily breakable. The disinfectant can be introduced through the opening 34 on top of the first chamber.

Figure 9B:
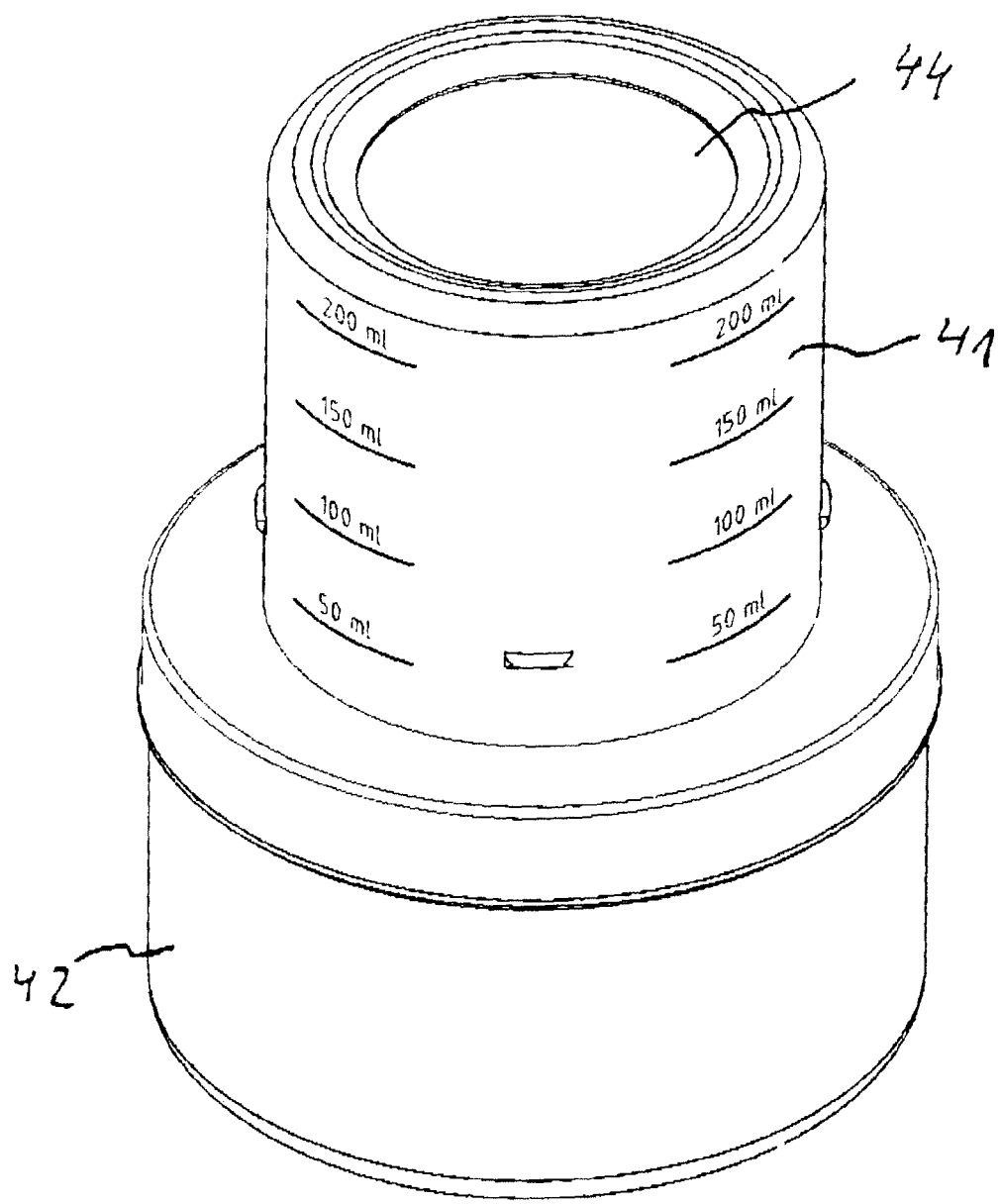
FIG. 9b shows the assembly of said component in a first position, namely the first chamber, the second chamber and the means for connecting the same. It is noted that the first chamber have a labelling on the outer surface representing predetermined amounts of volume to be filled in the first chamber.

FIG. 9 provides details of a further embodiment of the present invention. In particular, FIG. 9a shows an exploded view of the components of the disinfection system comprising a first chamber 41 a second chamber 42, means 43 for protecting undesired moving of the slidable connected chambers and covering the connecting parts of the first chamber and the second chamber, the first chamber has an opening 44 on top as well as labeling on the outside 47 indicating the volumes to be chargeable to the first chamber. Preferably, the first chamber is at least partly composed of a transparent material. The second chamber contains swabs to be impregnated with the disinfectant. FIG. 9b provides the assembly of the components shown in the exploded view of FIG. 9a in a first position where the swabs are not compressed and the bottom of the first chamber is not broken. By opening 44, e.g. the lug, the disinfectant can be introduced into the first chamber 41 by introducing a predetermined amount of disinfectant or introducing disinfectant following the labelling present on the outside of the first chamber. Not shown in FIGS. 9a and 9b, the second chamber has one or more pins or protrusions 47 which are preferably of conical shapes.

Figure 9C:
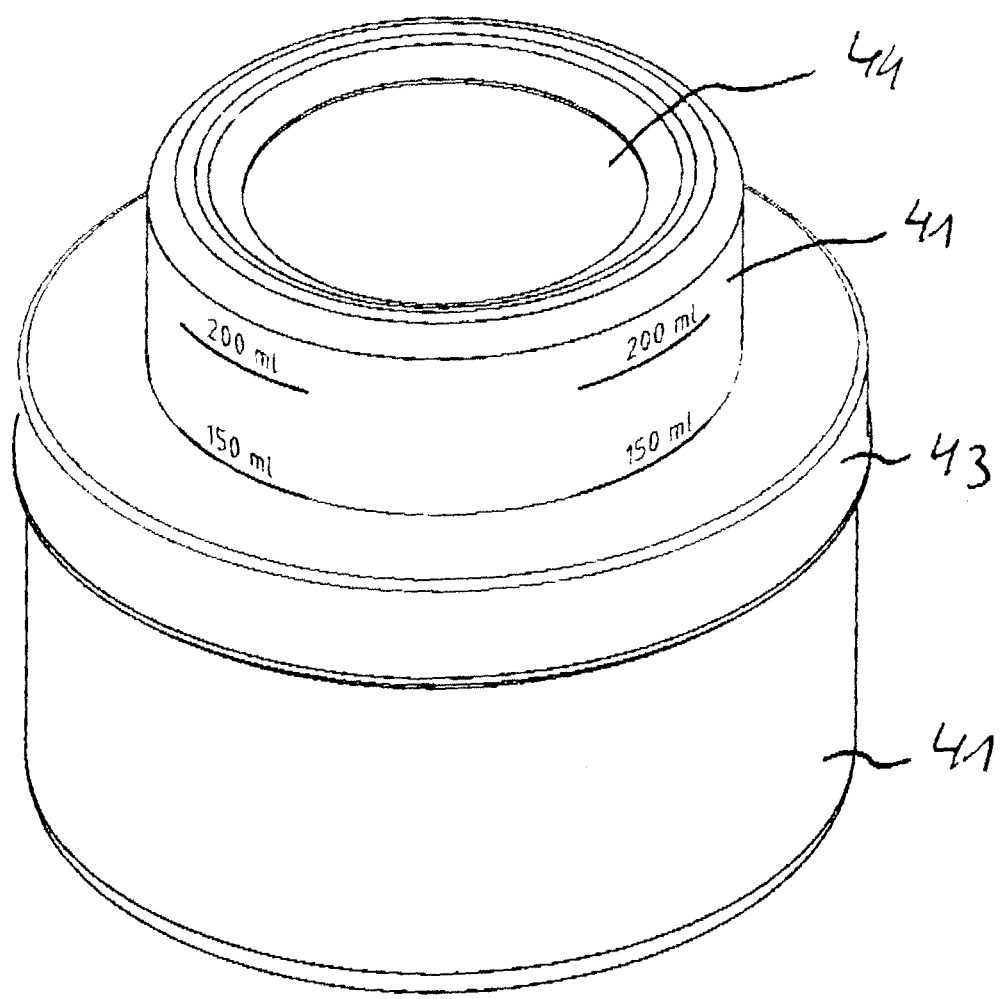
FIG. 9a is a perspective view showing an exploded drawing of a further preferred embodiment of the present invention. Similar to FIG. 8 a first chamber is provided mountable on the second chamber containing the swabs and a means for covering and connecting the first chamber with the second chamber.

FIG. 9c shows a system in a second position where the two chambers have been pressed such that the pin or the protrusions present in the second chamber 42 penetrated the bottom of the first chamber 41.

Figure 9E:
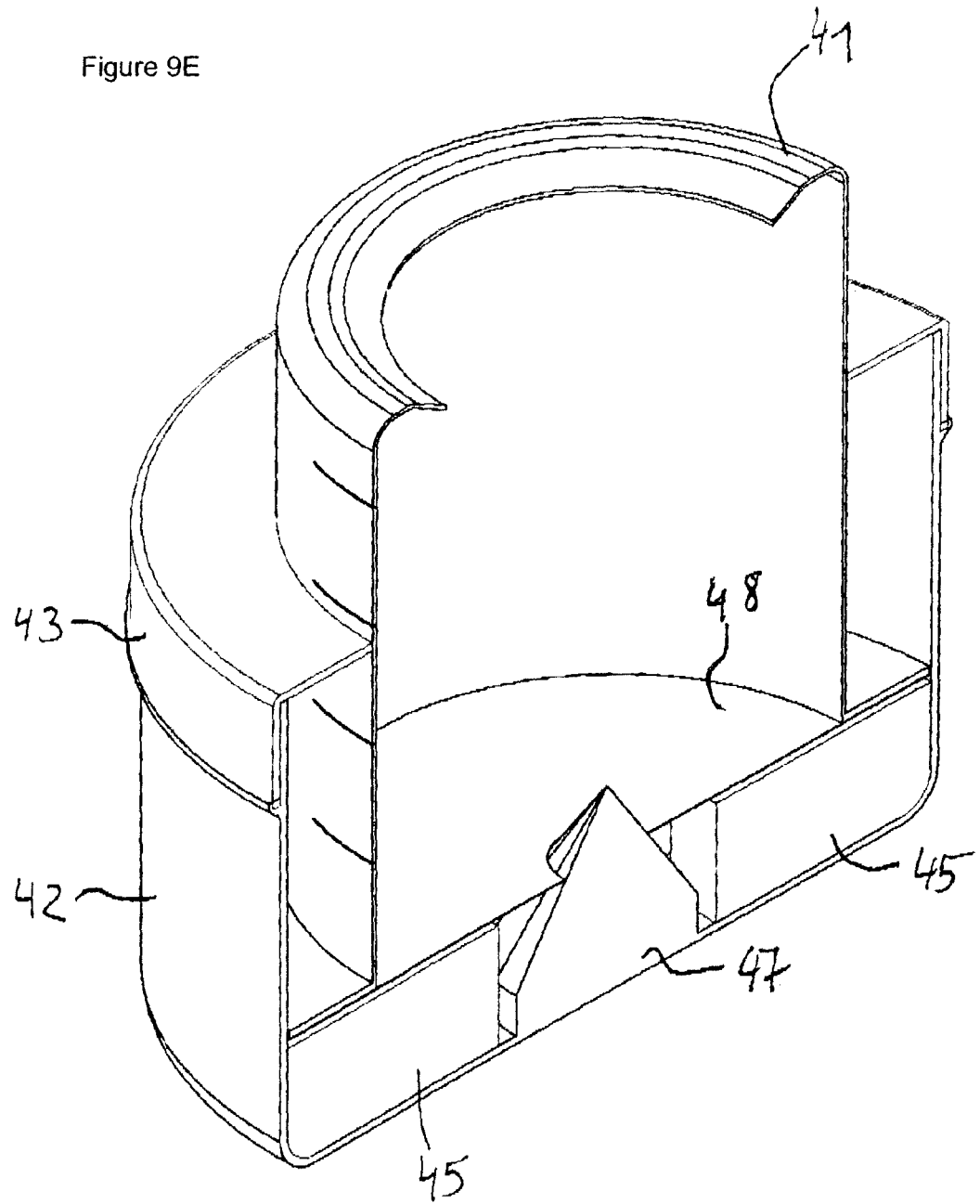

This is shown in more detail in FIGS. 9d and 9e showing a cross section of the system in a second position. Pin 47 which has a conical shape penetrates the bottom 48 of the first chamber 41 while swabs 45 are compressed in the second chamber 42. Disinfectant which is present in the first chamber 41 in a predetermined amount based on the labelling given on the outside of the first chamber may flow into the second chamber after depression of the chambers. When flowing into the second, lower chamber 42 the swabs 45 present in the lower chamber are impregnated with the disinfectant uniformly. The first chamber can be removed easily together with the means 43 and, thus, swabs are provided ready to use containing a defined amount of disinfectant.

The invention claimed is:

1. A disinfection system, comprising:
   (i) at least one first chamber and at least one second chamber, the at least one first chamber is adapted to contain a disinfectant and the at least one second chamber is adapted to store at least one swab and/or one sponge;
   (ii) at least one swab and/or sponge positioned in the at least one second chamber wherein said at least one swab and/or sponge is removable from the at least one second chamber for use in disinfecting a surface; and
   (iii) means for introducing the disinfectant from said at least one first chamber into the at least one second chamber,
   wherein the at least one first chamber and the at least one second chamber are connected to or are removably connectable to each other such that the disinfectant is directly or indirectly introduced into the at least one second chamber from said at least one first chamber by the means for introducing the disinfectant from the at least one first chamber into the at least one second chamber so as to saturate said at least one swab and/or sponge with a specified amount the disinfectant, and
   wherein the means for introducing the disinfectant from the at least one first chamber to the at least one second chamber comprises a protrusion or pin located in the at least one second chamber to be capable of penetrating a wall of said at least one first chamber, whereby a predetermined amount of the disinfectant from the at least one first chamber is introduced to the at least one second chamber upon penetration of said wall of said at least one first chamber.

2. The disinfection system according to claim 1, wherein the at least one swab and/or one sponge includes at least two swabs and/or sponges.

3. The disinfection system according to claim 1, further comprising at least one third chamber adapted to contain at least one swab and/or at least one sponge, said at least one third chamber is designed such that no disinfectant can be introduced into said at least one third chamber via an opening or passage from the at least one first chamber.

4. The disinfection system according to claim 1, wherein said at least one first chamber and said at least one second chamber are formed as a one piece container.

5. The disinfection system according to claim 1, wherein the at least one first chamber and the at least one second chamber are separated by a common wall and the common wall has a means for introducing the disinfectant from said at least one first chamber into said at least one second chamber at a weakened portion or a weak line capable of forming a through-hole or passage between said at least one first and said at least one second chamber.

6. the disinfection system according to claim 5, wherein the common wall has a predetermined or preformed breaking point.

7. The disinfection system according to claim 1, wherein the at least one first chamber contains the disinfectant and is relatively movable to the at least one second chamber from a first position to a second position such that when bringing the at least one first chamber into the second position the protrusion or pin of the at least one second chamber penetrates the wall of the at least one first chamber so that the disinfectant flows into the at least one second chamber.

8. The disinfection system according to claim 7, wherein the at least one first chamber and the at least second chamber are slidably connected.

9. The disinfection system according to claim 1, wherein the at least one first chamber and the at least one second chamber are separated by a common wall and the common wall has a means for introducing a disinfectant from the at least one first chamber into the at least one second chamber through at least one opening which is/are closed in a first position and which is/are open in a second position for introducing the disinfectant into the at least one second chamber.

10. The disinfection system according to claim 9, wherein the at least one opening is closed with a cover, wherein the cover is connected with a lid of a one piece container, in the first position and is detached from the opening when the lid is detached from the one piece container in the second position.

11. The disinfection system according to claim 1, further comprising at least two first chambers adapted for containing disinfectant, wherein at least two different disinfectants are contained in the at least two first chambers.

12. The disinfection system according to claim 1, wherein said at least one first chamber and said at least one second chamber are constructed so as to permit sterilization or autoclaving.

13. The disinfection system according to claim 1, further comprising a disinfectant present in the at least one first chamber in a predeteimined amount.

14. The disinfection system according to claim 1, wherein the disinfection system is configured for a single use.

15. A disinfection system, comprising:
   a first chamber containing a predetermined amount of at least one disinfectant, said first chamber having a bottom and a side wall;
   a second chamber containing at least two swabs or sponges and at least one projection for selectively creating an opening in said bottom of said first chamber; and
   a means for protecting undesired movement of said first chamber which holds said first chamber and said second chamber together in a first position,
   said side wall of said first chamber is sized to fit within said second chamber, and
   said means for protecting undesired movement of said first chamber permits said first chamber to be selectively moved within said second chamber causing said at least one projection to create said opening in said bottom of said first chamber whereby said predetermined amount of disinfectant is permitted to pass through said bottom of said first chamber and impregnate at least one swab or sponge, and wherein at least one of said at least two swabs or sponges is removable from said second chamber for use in disinfecting a surface.

16. The disinfection system of claim 15 wherein said first chamber is transparent.

17. The disinfection system of claim 16 further comprising indicia on said first chamber and wherein selected amounts of said at least one disinfectant can be stored in said first chamber with reference to said indicia.

18. The disinfection system of claim 15 wherein said at least one projection in said second chamber is conical in shape and is positioned at a base of said second chamber.

19. A disinfection system, comprising:
(i) at least one first chamber and at least one second chamber, the at least one first chamber is adapted to contain a disinfectant and the at least one second chamber is adapted to store at least one swab and/or one sponge;
(ii) at least one swab and/or sponge positioned in the at least one second chamber wherein said at least one swab and/or sponge is removable from the at least one second chamber for use in disinfecting a surface; and
(iii) a protrusion or pin located in said at least one second chamber to be capable of penetrating a wall of said at least one first chamber, whereby the disinfectant from the at least one first chamber is selectively introduced to the at least one second chamber upon penetration of said wall of said at least one first chamber,
wherein the at least one first chamber contains the disinfectant and is relatively movable to the at least one second chamber from a first position to a second position such that when bringing the at least one first chamber into the second position the protrusion or pin of the at least one second chamber penetrates the wall of the at least one first chamber so that the disinfectant flows into the at least one second chamber; and
(iv) a means for protecting undesired movement of the at least one first chamber while in said first position.

20. The disinfection system of claim 19 wherein said at least one swab and/or sponge includes at least two of said swabs and/or sponges.

21. A disinfection system, comprising:
(i) at least one first chamber and at least one second chamber, the at least one first chamber is adapted to contain a disinfectant and the at least one second chamber is adapted to store at least one swab and/or one sponge;
(ii) at least one swab and/or sponge positioned in the at least one second chamber wherein said at least one swab and/or sponge is removable from the at least one second chamber for use in disinfecting a surface; and
(iii) means for introducing the disinfectant from said at least one first chamber into the at least one second chamber; and
(iv) an element for displaying whether the disinfection system underwent sterilization,
wherein the at least one first chamber and the at least one second chamber are connected to or are removably connectable to each other such that the disinfectant is directly or indirectly introduced into the at least one second chamber from said at least one first chamber by the means for introducing the disinfectant from the at least one first chamber into the at least one second chamber so as to saturate said at least one swab and/or sponge with a specified amount of the disinfectant.

22. A disinfection system, comprising:
(i) at least one first chamber and at least one second chamber, the at least one first chamber is adapted to contain a disinfectant and the at least one second chamber is adapted to store at least one swab and/or one sponge;
(ii) at least one swab and/or sponge positioned in the at least one second chamber wherein said at least one swab and/or sponge is removable from the at least one second chamber for use in disinfecting a surface; and
(iii) means for introducing the disinfectant from said at least one first chamber into the at least one second chamber; and
(iv) a separate container adapted for external supplying a predetermined amount of the disinfectant to the at least one first chamber,
wherein the at least one first chamber and the at least one second chamber are connected to or are removably connectable to each other such that the disinfectant is directly or indirectly introduced into the at least one second chamber from said at least one first chamber by the means for introducing the disinfectant from the at least one first chamber into the at least one second chamber so as to saturate said at least one swab and/or sponge with a specified amount of the disinfectant.

\* \* \* \* \*